(12) United States Patent
Rines et al.

(10) Patent No.: US 6,444,219 B2
(45) Date of Patent: *Sep. 3, 2002

(54) ANTISEPTIC PACKAGED POLYVINYLPYRROLIDONE-CINNAMIC ALCOHOL SOLID PRODUCTS AND THE LIKE AND METHOD OF PREPARING THE SAME

(75) Inventors: Robert H. Rines; R. David Rines, both of Concord, NH (US)

(73) Assignee: Allor Foundation, Concord, NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/169,756

(22) Filed: Oct. 9, 1998

(51) Int. Cl.$^7$ .......................... A61F 13/00; A61L 15/00; A61L 15/16; A61K 9/70; A01N 25/00

(52) U.S. Cl. .................. 424/443; 424/443; 424/405; 424/400; 424/445; 424/446; 517/730; 517/733; 206/828

(58) Field of Search ................ 424/405, 443, 424/445, 446, 447, 400; 206/828; 514/730, 733

(56) References Cited

U.S. PATENT DOCUMENTS

| | | | |
|---|---|---|---|
| 3,525,340 A | | 8/1970 | Gilbert |
| 3,777,016 A | | 12/1973 | Gilbert et al. |
| 4,094,967 A | * | 6/1978 | Gilbert ........................ 424/28 |

OTHER PUBLICATIONS

Schwartz et al, Remington: the science and practice of pharmacy, pp 1873–1878, 1995.*

* cited by examiner

Primary Examiner—Russell Travers
Assistant Examiner—Shahnam Sharareh

(57) ABSTRACT

A method of rendering antiseptic a packaged solid admixed emulsion for treating bleeding cuts and the like containing, dispersed therein, a bactericidal component that is solid at room temperature, such as cinnamic alcohol, but melts or liquefies at blood temperature upon contacting the blood, comprising elevating the temperature of the packaged emulsion and/or contacting with moisture briefly to commence such liquefying to wet the exterior surface of the solid emulsion, and with concurrent release of bactericidal vapor within the package, and the resulting antiseptic solid emulsion products produced thereby.

10 Claims, 3 Drawing Sheets

Figure 1A:
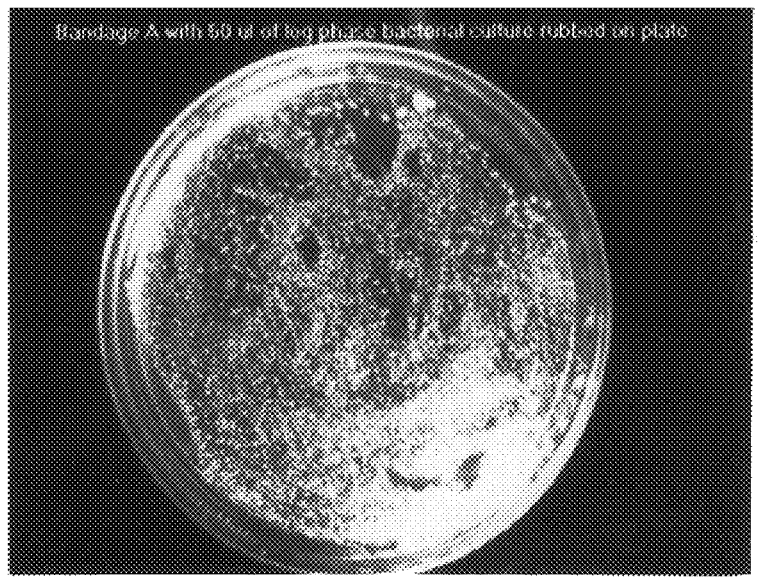

ANTISEPTIC PACKAGED POLYVINYLPYRROLIDONE-CINNAMIC ALCOHOL SOLID PRODUCTS AND THE LIKE AND METHOD OF PREPARING THE SAME

The present invention is directed to methods of and products for enabling the disinfecting or antiseptic protecting and substantially room temperature storing of normally dry bacterial-component-containing solid emulsions for pharmacological use with bleeding cuts, wounds, and abrasions and the like, being more particularly concerned with the rendering antiseptic during packaged or other storage of such dry solid emulsions of the type that start to melt, sublime or liquefy at somewhat higher than room temperature, (as of the order of the temperature of human or animal blood in living subjects—about 98–100° F.), upon being contacted by moisture, such as complexes of polyvinylpyrrolidone admixed with cinnamic alcohol and tannic acid, as described in U.S. Pat. Nos. 3,525,340 and 3,777,016 of Joseph G. Gilbert, and in U.S. Pat. No. 4,094,967 of the Allor Foundation, common assignee of the present invention.

BACKGROUND

In the first two of the above-referenced Gilbert patents, there is described a process of preparing such a solid emulsion complex of polyvinylpyrrolidone admixed with cinnamic alcohol and tannic acid (and with iodine admixed in the third patent), wherein the solid emulsion, as applied to a flexible or foam or other bandage substrate, or to a swab or in solid powder state, is applied to bleeding cuts (lacerations, wounds, etc.) and abrasions and the like, and commences melting or liquefying from the exterior surfaces at the elevated temperature of the blood upon contacting the bleeding cut or the like. This action releases the melting or liquefying active anti-bacterial cinnamic alcohol from the solid complex, and independently, active fungicidal tannic acid, that has been found remarkably to prevent infections, and, particularly through the film-forming and coagulation-binding of the polyvinylpyrrolidone, promotes rapid healing and, surprisingly, substantially without keloid formation.

Earlier culture tests demonstrating efficacy against pathological organisms, animal clinical tests, and substantial human subject clinical use are described particularly in the before-cited U.S. Pat. No. 3,777,016.

Because of the elevated-temperature-induced and/or moisture liquefying release and/or subliming by the blood in the wound of the bactericidal component (cinnamic alcohol) at the exterior surface of the solidified emulsion product upon use, it was thought that concerns about antiseptic packaging were no longer necessary. This had been considered a radically new feature of this novel product in that it did not have to be kept sterile or even packaged, because, substantially instantaneously upon use, the wound was immersed in released bacterial liquid melted from the solid emulsion—and, indeed, as stressed in the first two of the above patents, it was found no longer necessary, from an infection point of view, to be concerned even with careful cleansing of the skin at the wound area before applying the dressing.

In retrospect, however, this turned out to be too radical a concept for acceptance by the medical and health-care-providing community which had and has the ingrained concept of universal aseptic products and packaging whether really needed or not. The terms "packaging" and "package" are herein generically used to embrace envelopes, wrappings and other containments or coverings.

But the nature of this type of heat and moisture meltable or liquefying solidified emulsion complex, unfortunately, did not tend itself to any of the conventional high temperature auto-cleaving, ethylene oxide treatment, extended ultra violet, or other aseptic packaging and storing techniques customarily used for other products, in view of the deleterious physical and chemical effects of such procedures upon such emulsions.

It was not until the discovery underlying the present invention, indeed, that an effective and inexpensive disinfecting or antiseptic packaging technique was finally evolved, that is particularly tailored to, and inherently self-generating with the heat—and moisture-meltable or liquefying characteristics of the room temperature dry solid emulsion products hereinvolved, requiring no autoclaves or similar conventional sterilizing technique treatments, and that now promises to make these products commercially acceptable in the health-care industry.

OBJECTS OF INVENTION

It is accordingly an object of the present invention to provide a new and improved method of rendering such bactericidal-component-containing solid emulsion complexes antiseptic along their exposed surfaces and/or within packages enclosing the same, and providing resulting novel antiseptic solid emulsions.

Other and further objects will be explained hereinafter and are more fully delineated in the appended claims.

SUMMARY

In summary, from one of its important aspects, the invention embraces in the preparation of a normally room-temperature-stored package containing a normally dry bactericidal-component-dispersed solid emulsion complex (such as a cinnamic alcohol component, for example) for pharmacological use with bleeding cuts and abrasions and that remains solidified at room temperature and below and so long as it is not contacted by moisture, but that starts to liquefy at somewhat higher temperature of the order of the temperature of human or animal blood in a living subject upon application of moisture thereupon, a method of rendering antiseptic both the exposed surface of the solidified emulsion and the interior of the package, that comprises, treating the interior of the package with one or both of increased temperature, at least to said higher temperature, and applied moisture to said exposed surface, and, doing so only for a time interval that is limited to the time required for the commencement of liquefying of said component sufficiently to wet the exposed surface of the solidified emulsion from which the component is drawn, and with a concurrent resulting commencement of release of bactericidal vapor therefrom, and, returning the package to room temperature, and sealing the package from further moisture, to enable the drying and re-solidifying of the exposed surface of the emulsion after having been thus wetted with the bactericidal component liquid drawn therefrom, and with the interior of the package having been exposed to the released bactericidal vapor.

Preferred and best mode techniques, modifications and products will be described hereinafter in detail.

DRAWINGS

Figure 3A:
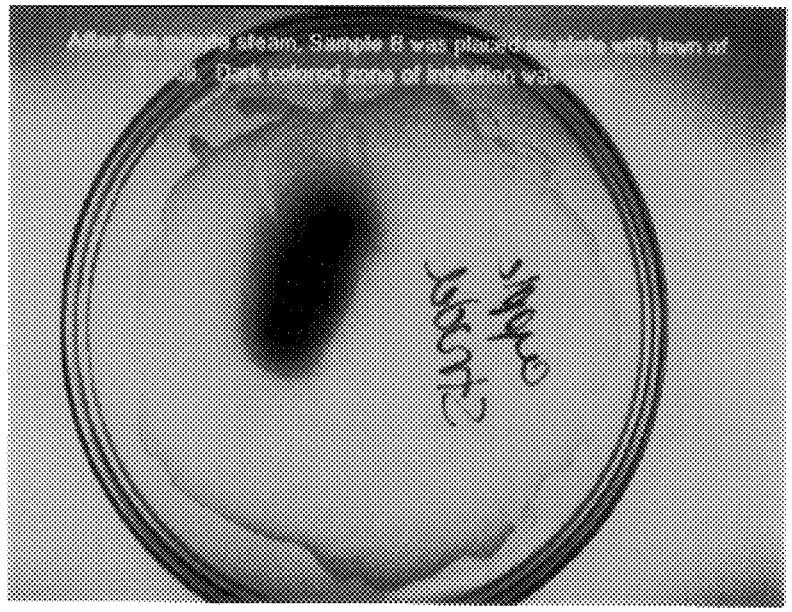
Figure 3B:
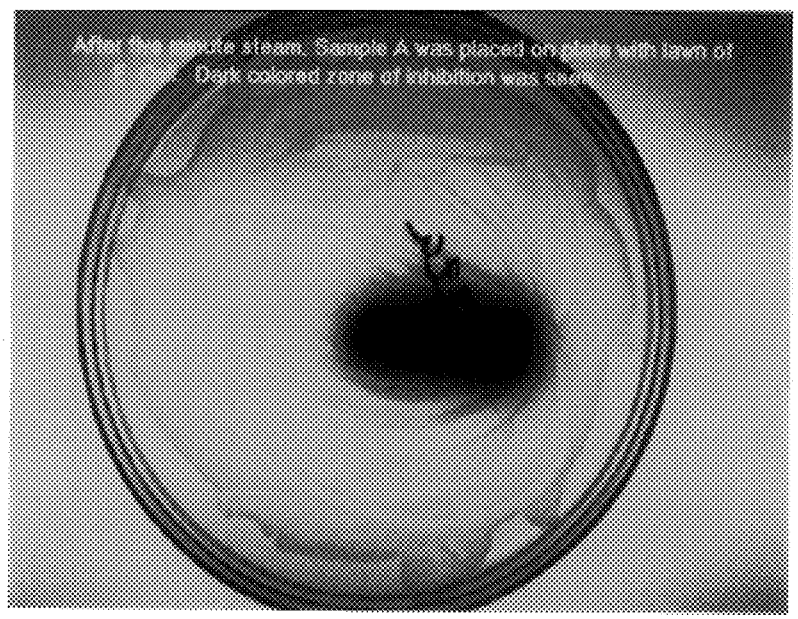

The invention will now be described in connection with the accompanying drawings, FIGS. 1A and 1B and 2A and 2B of which are photographic reproductions of bacteria-contaminated emulsion complex and antiscepticized emulsion complex surfaces of samples A and B, respectively, showing the sterilization by the process of the invention, and FIGS. 3A and 3B are zone of inhibition photographs further illustrating the sterilizing effects of the invention on samples A and B

PREFERRED EMBODIMENTS(S)

Underlying the present invention, is the discovery that, by causing the commencement of melting (including some sublimation) or liquefying—these words being used substantially synonymously herein—at the exposed surface of the bactericidal-component-containing solid admixed emulsions of the above-described type with which the present invention is concerned, as by short and slight temperature rise to the melting temperature of said component, and upon introduced moisture contact, as by steam or otherwise, bactericidal liquid starts to be drawn from and released through the exposed surface, wetting the same, this liquefying wetting process also releasing some vapor phase bactericidal vapor adjacent such surface and within the interior of the package in which the solid emulsion product may be contained. By terminating the heat/moisture and its surface liquefying and vapor release just after the commencement thereof, (as by rapidly removing or lowering the temperature and/or sealing against further moisture), and thus restoring the emulsion to its normal solid room-temperature dry state within the package, the exterior surface becomes totally re-solidified, but now with a self-generated antiseptic bactericidal coating on its exposed surface, and the interior of the package has been rendered antiseptic by the exposure to the antiseptic bactericidal vapor released therein during and as a result of the short-period melting transition from solid to liquid (wetting).

More specifically, the before-described solid emulsions of admixed polyvinylpyrrolidone-cinnamic acid-tannic acid (and/or iodine) have been successfully so rendered antiseptic both for containment in packages and without packages by this technique of the invention.

While as shown in above-cited patents, the complex of the invention is effective against a wide range of microorganisms for purposes of hereinafter described tests, *E. coli* was selected for illustrative use because of its current tenacity and pervasive problems, though the effects herein have also been observed on other microorganisms, including as described in said patents.

EXAMPLE 1

A sample solid emulsion of the above-described type (sample A) was prepared in the manner described in said Gilbert patents. A mixture was prepared from 2.92 g. tannic acid powder U.S.P., 0.71 g. cinnamic alcohol powder, and 28.32 g. polyvinylpyrrolidone sold by the GAF corporation under the trade designation K29–32; that is, a mixture of about 8.8 parts tannic acid, about 2.1 parts cinnamic alcohol, and about 85 parts polyvinylpyrrolidone, by weight. The mixture was dissolved in 22.5 ml. water during agitation in a Waring blender, and the resulting viscous, yellowish solution was spread with a spatula over one side of a 3/32 inch thick white foam rubber webbing. About 29.6 ml. solution covered about 258 cm.² of the substrate. After drying at room temperature, a thin, pale-yellowish, dry-to-touch film was obtained as the residue of the solution. (Such coated foam rubber webbing was earlier successfully used by Dr. Gilbert in the infirmary of a manufacturing plant for the successful treatment of over 160 lacerations of varying sizes and types).

Sample A was exposed for at least several months to the atmosphere without ally packaging. It was then subjected briefly to steam until the surface was observed to start to liquefy or become wet and a distinctive "cinnamon" vapor was released (from 30 seconds to 5 minutes). After drying in air, the sample was swabbed over a tryptone and yeast extract agar growth medium (luria broth—LB extract). It was then incubated at 37° C. overnight. No bacterial growth was observed.

EXAMPLE 2

The preparation technique of Example 1 was used in a sample B prepared with iodine crystals in an alcohol base (ethanol) added to the mixture before drying, as taught in before-mentioned U.S. Pat. No. 4,094,967, namely, polyvinylpyrrolidone K30 (28.349 grams) was dissolved in 19 cc of water by agitation, using slow mixing. Finely powdered crystalline iodine (1 gram) was dissolved in 15 cc of 95% alcohol (ethanol) and added to the wetted (emulsified) polyvinylpyrrolidone and slowly mixed thoroughly. 2 grams of liquid cinnamic alcohol (solid form melted at about 100° F.) was added to the above and slowly agitated. Powdered tannic acid (2 grams) was then added to the above and mixed uniformly therein to form an emulsion. The emulsion was then uniformly spread on a polyester dressing about 36 inches square and was permitted to air dry at substantially room temperature to evaporate the solvents and moisture to form an adherent unitary solid coating.

Sample B, after standing for at least several months exposed to the atmosphere without any packaging, was briefly steamed to the commencement of surface liquification and cinnamic alcohol vapor release and then dried, swabbed over the agar of Example 1 and incubated overnight. No bacterial growth was observed.

EXAMPLES 3 AND 4

The same protocols described under Examples 1 and 2 for samples A and B, were performed, but with each sample intentionally contaminated with 10 μl of *E. coli* before steam surface liquefying and vapor release, drying and swabbing over the agar. No growth was observed for either samples A or B.

EXAMPLES 5 AND 6

Figure 1B:
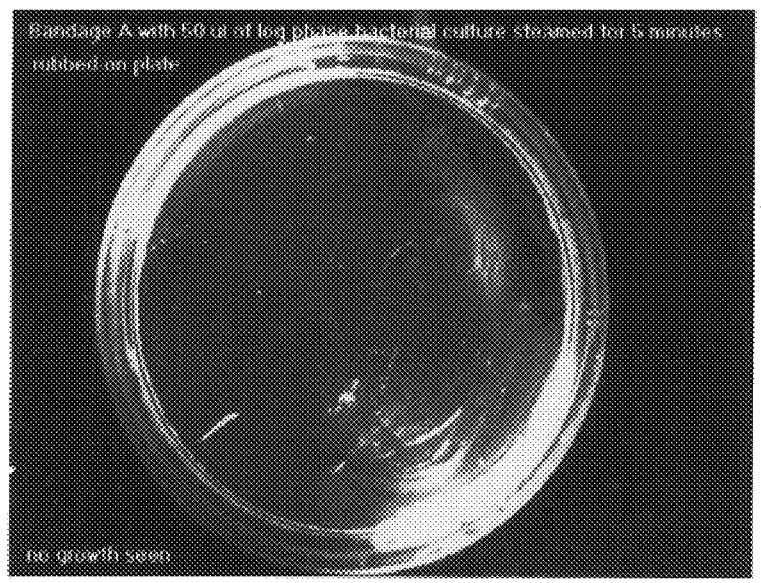
Figure 2A:
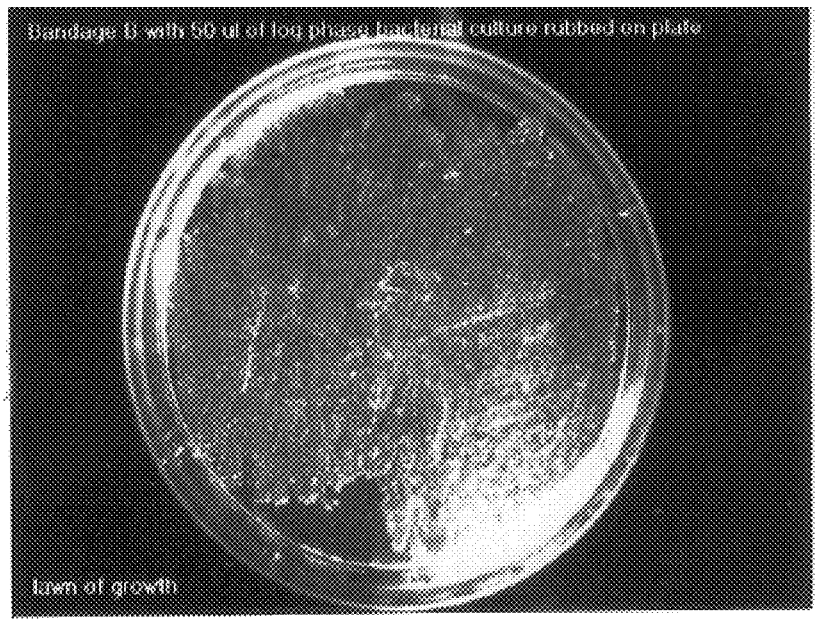
Figure 2B:

The same protocol with two pieces each of samples A and B contaminated with 50 μl of log-phase bacterial culture of *E. coli* (i.e. live growing bacteria). One piece of each of samples A and B was used as a control and swabbed over the agar without liquefying activation. A considerable lawn of bacterial growth was found to develop during overnight incubation, as shown in FIG. 1A for control sample A and FIG. 2A for control sample B. The other pieces of each of samples A and B, so contaminated, were activated by brief steam surface liquefying, allowing the liquid coating to dry, with the coating sealing the surface, and then swabbed over the agar. No bacterial growth whatsoever was observed during or after the overnight incubation, as shown in FIG. 1B for activated sample A and FIG. 2B for sample B.

These experiments demonstrated that the brief steam (heat-moisture) surface-liquification process sterilized the surface of the bandages. They did not, of themselves, however, demonstrate whether the heat itself played any part in inhibiting the bacterial growth as distinguished from the bactericidal effect of the liquefied cinnamic alcohol released at and wetting the surface

EXAMPLES 7 AND 8

To ascertain the answer to this question, the tested samples A and B of experiments 3 and 4 were then re-activated to surface liquification commencement, and were then applied to agar plates growing *E. coli* and which were not subjected to steam or other heat. Zones of inhibition clearly and sharply developed around both bandage samples, A and B (FIGS. 3A and 3B). These indicated two results: one, that the observed bactericidal sterilizing property of the surface-liquefying process was inherent to and solely caused by the release of the bactericidal component upon liquification and vapor release of the cinnamic alcohol-bound-surface and not to exposure to heat; and secondly, that the thusly sterilized bandage can be readily re-used with retained bactericidal efficacy.

This discovery enables repeated sterilizations of exposed emulsion surfaces, whenever desired, and without any degrading of the bactericidal efficacy for use on cuts and wounds when needed. Where packaged, re-sterilization of packages inadvertently torn or opened is thus also readily achievable.

EXAMPLE 9

Bandage strips like sample A, about 2" long by ½" wide were cut and inserted in closely fitting paper envelope packages of but slightly larger dimensions, and sealed with external tape. (Self or pressure-release adhesive flaps could have been used.)

The packaged dry solid-emulsion coated strips were then, in accordance with the present invention, heated with a hair-dryer-type blower until it was observed that the exterior coating surface was becoming slightly wet or moist, starting some melting or liquefying, demonstrated in Examples 1, 3 and 5 to achieve self-sterilization (FIGS. 1B and 3A). The distinct odor of cinnamic alcohol vapor was again immediately noticed, demonstrating the release of such bactericidal vapor within the package and permeating the interior of the paper package.

The heat was thereupon removed and the packages allowed rapidly to cool back to room temperature (more slowly in air, and more rapidly by a short stay in the refrigerator) with the melted or liquefied wetting coating formed on and from the emulsion appearing totally re-solidified and dry, and with the surface sealed by the coating.

EXAMPLE 10

Samples prepared as in Example 1, above, (sample A), were placed in the paper packages after being subjected to a fine spray of water (droplets on the emulsion) and slightly rubbed against the emulsion. Commencement of oozing of cinnamic alcohol from the complex to the surface, was again observed, accompanied by its vapor phase release, evident by smell. The packages were then externally sealed by taping to insure no further introduction of moisture. Both standing and accelerated drying with a blast of heat returned the emulsion to its dry state once more, with the wetted coating dried thereon, and providing the same antiseptic results as in Example 6.

EXAMPLE 10

The procedure of Example 9 was repeated, but, in addition to the slight moisturizing, heat was also applied from the hair dryer for a few seconds, accelerating the commencement of release of liquefied cinnamic alcohol and its vapor.

Once the packaged solid emulsion is rendered antiseptic as above described, it may be stored at room temperature until the bandage is to be used, whereupon the package is opened and the coated bandage is ready for use, as in the manner reported in the last-named patent. In the use of sample B, for example, placing the coating on a bleeding wound has been found to melt the solidified cinnamic alcohol and release active iodine, active anti-bacterial cinnamic alcohol, and independently active fungicidal tannic acid. Tests for the continuous slight heat and/or moisture release of these ingredients were performed, with the following simple visual and olfactory observations demonstrating the above, to wit, rubbing the moist coating on a starch-containing paper shows the purple active iodine, the yellow tannic acid, and with the aromatic characteristics of the cinnamic alcohol being clearly evident.

EXAMPLE 11

The process of Example 10 was repeated without the tannic acid.

EXAMPLE 12

The antiscepticizing processes of Examples 1–4 may be carried out with solid emulsion constituent weight proportion ranges of substantially the following. polyvinylpyrrolidone. 82–90%, cinnamic alcohol, 3–15%, and tannic acid, 3–12%, and, for Examples 2 and 4, iodine ½–3%

EXAMPLE 13

The process of Example 1 was repeated (sample A), but with the solid emulsion coating formed on a ceramic surface and then ground thereupon to form a fine powder of solid particles, sealed in the paper package, and rendered antiseptic as above.

EXAMPLE 14

Example 10 was repeated but with the solid emulsion complex formed as a coating at and sealing the end of a swab and sealed in the package.

EXAMPLE 15

The materials as in Examples 1–4, samples A and B, were treated without the use of individual packages, but with the moisture (and heat) applied, and either dried or left moist, before use of the product to provide an antiseptic outer surface.

While the above preferred constituents have been found very effective, for various therapeutic purposes, additional and/or substitute components may, as taught in U.S. Pat. No. 3,777,016, be employed, including, for example, substituting for an equal amount of polyvinylpyrrolidone, 0.25–1 parts by weight, (preferably about 0.5 part by weight, solid basis) of cortisone or cortisone derivative to promote healing, 0.5–2 parts by weight, (preferably about 0.7 part by weight, solids basis), of benzocaine or xylocaine to obtain increased analgesic action, and 0.04–0.09 part by weight, solid basis of benzalkonium chloride, if supplementation is desired, of the antibacterial action of the basic active composition.

Clearly, other types of packages and package materials and formats may be employed for the solid emulsion complexes of the invention and may similarly be rendered antiseptic, or the products may be otherwise stored for use and rendered antiseptic before use, and other modifications will also suggest themselves to those skilled in the art, such being considered to fall within the spirit and scope of the invention as defined in the appended claims.

What is claimed is:

1. A method of antiseptically packaging articles for room-temperature dry storage, the method comprising inserting a bactericidal-component-dispersed solidified emulsion complex having surfaces that liquefy upon contacting human or animal blood temperatures of about 98–100° F. in a living subject within the interior of an outer package; exposing said surfaces of the solidified emulsion and the interior of the package to said elevated temperatures and/or to moisture sufficient to start the liquefying of said bactericidal component of the solidified emulsion and the releasing of bactericidal vapor generated from said liquefying; and upon the start of vapor release, terminating said liquefying and returning the temperature to room temperature to resolidify said surfaces; and, if the package is not already sealed, sealing said package.

2. The method as claimed in claim 1 wherein said solidified emulsion is formed by dissolving a mixture comprising polyvinylpyrrolidone and cinnamic alcohol in water, and then drying to the resulting mixture solid form at about room temperature, with the cinnamic alcohol serving as said bactericidal component.

3. The method as claimed in claim 2, wherein tannic acid is added to said mixture before emulsifying polyvinylpyrrolidone and cinnamic alcohol emulsification.

4. The method as claimed in claim 3 wherein the weight percentages of the constituents of the solidified emulsion are substantially within the ranges: polyvinylpyrrolidone, 82–90%, cinnamic alcohol, 3–15%, and tannic acid, 3–12%.

5. The method as claimed in claim 4 wherein the polyvinylpyrrolidone is provided in water solution and the cinnamic alcohol is added in liquid form.

6. The method as claimed in claim 2 wherein an alcohol or aqueous solution of iodine is added to the mixture.

7. The method as claimed in claim 6 wherein the weight percentage of the iodine is substantially in the range: ½–3%.

8. The method of claim 1 wherein the temperature and moisture are applied by steam.

9. The method of claim 1 wherein said solidified emulsion complex surfaces are of solid dry admixed polyvinylpyrrolidone-cinnamic-alcohol complex.

10. The method of claim 1 wherein said complex further includes one or both of tannic acid and iodine.

* * * * *